United States Patent
Kirsch

(10) Patent No.: US 11,980,456 B2
(45) Date of Patent: May 14, 2024

(54) DETERMINING A PATIENT MOVEMENT DURING A MEDICAL IMAGING MEASUREMENT

(71) Applicant: Siemens Healthcare GmbH, Erlangen (DE)

(72) Inventor: Rainer Kirsch, Baiersdorf (DE)

(73) Assignee: Siemens Healthineers AG, Forchheim (DE)

(*) Notice: Subject to any disclaimer, the term of this patent is extended or adjusted under 35 U.S.C. 154(b) by 67 days.

(21) Appl. No.: 16/912,898

(22) Filed: Jun. 26, 2020

(65) Prior Publication Data
US 2020/0405179 A1    Dec. 31, 2020

(30) Foreign Application Priority Data
Jun. 26, 2019   (EP) .................................... 19182647

(51) Int. Cl.
| | | |
|---|---|---|
| *A61B 5/055* | (2006.01) | |
| *A61B 5/00* | (2006.01) | |
| *A61B 90/00* | (2016.01) | |
| *G06N 20/00* | (2019.01) | |

(52) U.S. Cl.
CPC .............. *A61B 5/055* (2013.01); *A61B 5/004* (2013.01); *A61B 90/39* (2016.02); *G06N 20/00* (2019.01); *A61B 2090/3954* (2016.02)

(58) Field of Classification Search
CPC ............ A61B 5/721; A61B 2034/2055; A61B 5/1128; A61B 2034/2065
See application file for complete search history.

(56) References Cited

U.S. PATENT DOCUMENTS

| | | |
|---|---|---|
| 2005/0203373 A1 | 9/2005 | Boese |
| 2010/0063419 A1 | 3/2010 | Mostafavi |
| 2012/0170824 A1 | 7/2012 | Hendriks |
| 2013/0211261 A1 | 8/2013 | Wang |
| 2013/0230228 A1 | 9/2013 | Leung |
| 2013/0342851 A1 | 12/2013 | Dresel |

(Continued)

FOREIGN PATENT DOCUMENTS

| | | |
|---|---|---|
| CA | 2839854 A1 | 7/2015 |
| CN | 1647758 A | 8/2005 |

(Continued)

OTHER PUBLICATIONS

Slipsager et al., "Markerless motion tracking and correction for PET, MRI, and simultaneous PET/MRI," (Apr. 19, 2019) PLoS ONE 14(4): e0215524. (Year: 2019).*

(Continued)

*Primary Examiner* — Joel Lamprecht
*Assistant Examiner* — Ashish S Jasani
(74) *Attorney, Agent, or Firm* — Lempia Summerfield Katz LLC

(57) ABSTRACT

A method for determining a patient movement during a medical imaging measurement with an imaging apparatus, a computer-implemented method for providing trained functions, an imaging apparatus, and a computer program product are provided. The method for determining the patient movement provides that reference image data of a body region, such as a head region, of a patient is acquired and the patient movement is determined with the aid of the reference image data.

18 Claims, 5 Drawing Sheets

(56) References Cited

U.S. PATENT DOCUMENTS

| | | |
|---|---|---|
| 2014/0070807 A1 | 3/2014 | Biber |
| 2014/0073904 A1 | 3/2014 | Biber |
| 2014/0159721 A1* | 6/2014 | Grodzki ............... G01R 33/48 324/309 |
| 2015/0016682 A1 | 1/2015 | Levy |
| 2015/0036911 A1 | 2/2015 | Brenner |
| 2015/0139515 A1 | 5/2015 | Smith |
| 2015/0164440 A1 | 6/2015 | Rackow |
| 2015/0366527 A1* | 12/2015 | Yu ............... A61B 6/527 600/407 |
| 2016/0038090 A1 | 2/2016 | Heismann |
| 2016/0247293 A1 | 8/2016 | Beylin |
| 2016/0278731 A1 | 9/2016 | Babic |
| 2016/0379353 A1 | 12/2016 | Makifuchi |
| 2018/0070904 A1* | 3/2018 | Yu ............... A61B 6/527 |
| 2019/0000318 A1 | 1/2019 | Caluser |
| 2020/0058389 A1 | 2/2020 | Saalbach |
| 2020/0113486 A1 | 4/2020 | Olesen |
| 2020/0206536 A1 | 7/2020 | Wang |
| 2020/0302619 A1* | 9/2020 | Lu ............... G06T 7/521 |

FOREIGN PATENT DOCUMENTS

| | | |
|---|---|---|
| CN | 102421365 A | 4/2012 |
| CN | 102883655 A | 1/2013 |
| CN | 103445865 A | 12/2013 |
| CN | 103654784 A | 3/2014 |
| CN | 104603835 A | 5/2015 |
| CN | 104706424 A | 6/2015 |
| CN | 105361955 A | 3/2016 |
| CN | 105578985 A | 5/2016 |
| CN | 106955122 A | 7/2017 |
| CN | 107095678 A | 8/2017 |
| CN | 109464757 A | 3/2019 |
| CN | 109937012 A | 6/2019 |
| DE | 102012216292 A1 | 5/2014 |
| EP | 3069660 A1 | 9/2016 |
| EP | 3477583 A1 | 5/2019 |
| JP | 2017127578 A | 7/2017 |
| WO | 2019029934 A1 | 2/2019 |
| WO | WO-2020077198 A1 * | 4/2020 |

OTHER PUBLICATIONS

Frost et al., "Markerless high-frequency prospective motion correction for neuroanatomical MRI," (Feb. 28, 2019), Magnetic Resonance in Medicine, vol. 82, Issue 1, p. 126-144. (Year: 2019).*

Wang et al., "Deep Closest Point: Learning Representations for Point Cloud Registration," (May 8, 2019), arXiv:1905.03304. (Year: 2019).*

Kyme et al., "Markerless motion estimation for motion compensated clinical brain imaging," (May 17, 2018), Phys. Med. Biol. 63 (2018) 105018 (17pp). (Year: 2018).*

Kyme, Andre Z., et al. "Feasibility of marker-free motion tracking for motion-corrected MRI and PET-MRI." 2016 IEEE Nuclear Science Symposium, Medical Imaging Conference and Room-Temperature Semiconductor Detector Workshop (NSS/MIC/RTSD). IEEE, 2016, pp. 1-3.

Liu Fengxia et al.:"Methods of MRI artifacts and image optimization process", China Prac Med, Oct. 2011, vol. 6, No. 30, with English Translation. pp. 1-6.

* cited by examiner

DETERMINING A PATIENT MOVEMENT DURING A MEDICAL IMAGING MEASUREMENT

This application claims the benefit of European Patent Application No. EP 19182647.8, filed on Jun. 26, 2019, which is hereby incorporated by reference in its entirety.

BACKGROUND

The present embodiments relate to determining a patient movement during a medical imaging measurement with an imaging apparatus.

Movements of a patient during a medical imaging measurement (e.g., with magnetic resonance imaging (MRI) or computed tomography (CT)) may be of interest for a variety of reasons. For example, patient movements may cause motion artifacts in resulting images of the patient. These may be reduced when the patient movements are known.

SUMMARY AND DESCRIPTION

The scope of the present invention is defined solely by the appended claims and is not affected to any degree by the statements within this summary.

The present embodiments may obviate one or more of the drawbacks or limitations in the related art. For example, patient movement may be reliably and/or rapidly determined during a medical imaging measurement.

A method for determining a patient movement during a medical imaging measurement with an imaging apparatus is thus provided. Reference image data of a body region (e.g., a head region) of a patient is acquired, and the patient movement is determined with the aid of the reference image data. The acquisition of the reference image data may take place, for example, with one, for example, optical camera.

Medical imaging data that is particularly suited to generating diagnostic images of the patient therefrom may be acquired during the medical imaging measurement. At least one image of the patient may be produced based on the medical imaging data and the determined patient movement. Such medical imaging data may be, for example, magnetic resonance signals, from which magnetic resonance images may be reconstructed. Medical imaging data may be corrected based on the determined patient movement. The reference image data may be optical data (e.g., acquired optically; by optical light).

The imaging apparatus may be a magnetic resonance apparatus. Magnetic resonance measurements last for a comparatively long time, which is why patient movements occurring can have a particularly significant effect on magnetic resonance images. When patient movements are known, these may advantageously be effectively compensated.

For example, an ongoing imaging measurement (e.g., a sequence of a magnetic resonance measurement) may be adjusted prospectively based on the determined patient movements. In addition or alternatively, measured medical imaging data (e.g., magnetic resonance signals) may be corrected retrospectively based on the determined patient movements.

The patient may be, for example, a human or animal patient. For example, patient movements may be movements in the region of the head (e.g., of the face) of the patient.

The reference image data may include three-dimensional data (e.g., depth images) of the body region of the patient (e.g., the face).

One embodiment of the method for determining a patient movement provides that a reference model of the acquired body region of the patient is produced based on the reference image data. Patient image data of a part of the body region of the patient, for which reference image data has been acquired, is acquired during the medical imaging measurement (e.g., the acquired patient image data forms a part of the body region of the patient acquired by the reference image data). This part may not include the entire body region of the patient acquired by the reference image data. Adjustment data is produced from the patient image data. The patient movement is determined by adjusting the adjustment data to the reference model. A behavior (e.g., a movement) of the body region of the patient that is not acquired by the patient image data is determined by adjusting the adjustment data to the reference model.

The acquisition of the reference image data of the body region of the patient preferably takes place before the imaging measurement. The acquisition of the reference image data may take place, for example, using, for example, an optical camera that is independent of a recording unit of the imaging apparatus. Such an acquisition of the reference image data may take place, for example, before the patient is introduced into a bore of a magnetic resonance apparatus, in which magnetic resonance signals, which are acquired as medical imaging data, are generated.

In one embodiment, a camera for acquiring the reference image data may be arranged on the recording unit of the imaging apparatus (e.g., on and/or in a bore of a magnetic resonance apparatus).

The reference model may be a three-dimensional model (e.g., mathematical model). For example, the reference model includes a lattice model of the body region of the patient, which is described by spatially distributed lattice points.

Prior anatomical knowledge (e.g., independent of the specific patient, the patient movement of which is determined here) may be included in the reference model. Such prior knowledge may be, for example, an average face shape and/or face shape averaged among a plurality of people. The reference model may cover a region of the patient body that is larger than the part of the patient body that is acquired during the medical imaging measurement by the patient image data.

The acquisition of the patient image data may take place, for example, with one camera (e.g., optical camera). The patient image data is therefore, for example, optical data that is acquired by a camera using optical light. This camera may, for example, be the same as the one used to acquire the reference image data. This camera may, however, also be another camera. The camera for acquiring the patient image data may be arranged on the recording unit of the imaging apparatus (e.g., on and/or in) a bore of a magnetic resonance apparatus. For example, such a camera is arranged on the interior of the bore above the position in which the head of the patient is typically supported.

The acquisition of the patient image data may take place, for example, continuously during the medical imaging measurement. A continual acquisition of the patient image data may be a measurement, for example, during which images of the part of the body region of the patient are generated with a repetition frequency of 10 to 100 Hz (e.g., 60 Hz).

The patient image data may include, for example, three-dimensional data (e.g., depth images of the patient) of, for example, the face. For example, multidimensional (e.g., three-dimensional) adjustment data may be derived from three-dimensional patient image data, which may be adjusted particularly effectively to a three-dimensional reference model.

Adjustment of the adjustment data to the reference model may include, for example, a fitting or a regression of the adjustment data to the reference model. When the adjustment data is adjusted to the reference model, at least one part of the body region of the patient, which has not been acquired by the patient image data, may be reconstructed.

By adjusting the adjustment data to the reference model, the patient movement of the entire body region of the patient may be determined, although only one part of the body region is acquired during the medical imaging measurement. This may then be advantageous if this body region is partially covered. As a result, the body region is, for example, only acquired incompletely (e.g., with gaps).

For example, during the acquisition of the patient image data, the body region of the patient is partially covered by the imaging apparatus so that only one part of the body region is acquired by the patient image data during the medical imaging measurement.

The production of the adjustment data from the patient image data may, for example, include a direct and/or unchanged take-over of the patient image data. For example, the adjustment data may be identical to the patient image data. Alternatively, the adjustment data may be modified with respect to the patient image data.

A further embodiment of the method for determining a patient movement provides that an item of geometry information of a module of the imaging apparatus is provided. The module partially covers the body region of the patient during the acquisition of the patient image data, but, for example, not completely. Adjustment data is produced with the aid of the geometry information. The patient movement may then take place more accurately by taking the geometry information of the module into account.

The module of the imaging apparatus may, for example, be part of the imaging apparatus, which partially covers the body region of the patient during the acquisition of the patient image data. The module of the imaging apparatus may be, for example, a local coil. A local coil typically includes one or more antennas that are configured to send and/or receive radio frequency signals (RF). Local coils are typically arranged as close as possible to the patient in order to achieve a high signal-to-noise ratio of received magnetic resonance signals.

The acquired body region of the patient may be a head region of the patient, and the local coil is a head coil. The head coil may have one or more cutouts, so that only one part of the head of the patient is covered when the body coil is arranged on the patient. For example, the body coil includes a top part (e.g., anterior part) that has such cutouts.

A further embodiment of the method for determining a patient movement provides that the production of the adjustment data from the patient image data includes a production of differential image data from the geometry information of the module and the patient image data. The differential image data is used as adjustment data. The adjustment data may only include segments of the patient image data that have not been covered during the acquisition of the patient image data. For example, the geometry information is subtracted from the patient image data. The segments of the patient image data, which correspond to the geometry information of the module, may be identified and removed from the patient image data, for example.

The differential image data may be used to adjust the patient image data to the reference model and/or to determine the patient movement more accurately and/or reliably, since the patient-independent (e.g., immobile) parts of the patient image data have been removed.

A further embodiment of the method provides that the production of the differential image data from the geometry information of the module and the patient image data involves applying a function trained by machine learning to the geometry information of the module and the patient image data. Differential image data is generated. The function may be applied with the aid of a computer unit.

The geometry information may exist in a database, for example, in which geometry data (e.g., CAD data) relating to one or more modules is stored. Within the scope of the medical imaging measurement, the module that is to be used during the medical imaging measurement may be specified. Provision of the geometry information of the module may include retrieving this geometric data from the database, for example.

The provision of the geometry information of the module of the imaging apparatus may include an acquisition of module image data of the module of the imaging apparatus. The acquisition of the module image data may take place, for example, with one camera (e.g., an optical camera). This camera may, for example, be the same as the one also used to acquire the reference image data and/or patient image data. The camera may, however, also be another camera.

For example, a camera is used to record a top part of a body coil as module image data. During the medical imaging measurement, the top part of the body coil is recorded as patient image data together with the segments of the patient face that are visible between cutouts in the top part of the body coil. By subtracting the module image data from the patient image data and/or applying a trained function to the module image data and the patient image data, revised differential image data is obtained from the top part of the head coil. A behavior (e.g., a movement) of the entire field of vision of the patient (e.g., including the parts covered by the top part of the body coil) is determined by adjusting the differential image data to the reference model.

The module image data of the module may be recorded from the same perspective as the patient image data of the body region of the patient during the medical imaging measurement. This enables differential image data to be produced in a simple fashion.

The determination of the patient movement may take place in real time (e.g., immediately after acquiring the respective patient image data; by adjusting the adjustment data to the reference model). The patient movement information is therefore immediately available for further processing. For example, the determined patient movement is used for a functional magnetic resonance imaging and/or for movement correction.

A further embodiment of the method provides that the determination of the patient movement by adjusting the adjustment data to the reference model involves applying a function trained by machine learning to the adjustment data, where patient movement data is generated. The function may be applied with the aid of a computer unit (e.g., a computer including one or more processors).

A further embodiment of the method provides that the body region is a face of the patient, where the reference image data of the body region of the patient is acquired by a miniature camera arranged in a head coil.

For example, with the aid of a mini camera, the reference image data of the face may be recorded in real time, and the position and the movement of the head may be identified in real time without attaching external markers and may be used, for example, for movement correction. The reference image data is, for example, depth images.

Use may be made of three-dimensional face tracking algorithms, such as those used in mobile radio devices, for example. For example, three-dimensional lattice images may be produced in order to determine the patient movement therefrom.

No external marker may be attached to the patient (e.g., to the head of the patient) during the medical imaging measurement. One such external marker may be, for example, a marker, the acquisition of which is suited to determining a patient movement. For example, such an external marker may be a marker, the acquisition of which is suited to determining a movement of the body part to which the marker is attached. An external marker may be a field marker, for example.

The determination of the patient movement may take place in real time during the medical imaging measurement. As a result, the patient movement is reliably determined within a predetermined time frame (e.g., in a fixed time period). This predetermined time frame may amount to less than, for example, 10 seconds, less than 1 second, or less than 0.1 seconds.

In one embodiment, computer-implemented method provides a trained function in order to generate differential image data. This method includes receiving training module image data and training patient image data and receiving training differential image data. The training differential image data is, for example, linked to the training module image data and training patient image data. The method includes training a function based on the training module image data, the training patient image data, and the training differential image data and providing the trained function in order to generate differential image data.

The training module image data is data, for example, that images a module of an imaging apparatus. The training patient image data is data, for example, that images a region of the patient.

The trained function may be based on a neural network (e.g., a convolutional neural network (CNN) or a deep convolutional neural network).

For example, a training system that includes a first training interface for receiving training module image data, a second interface for receiving training patient image data, and a third interface for receiving training differential image data is provided. The training system also includes a training calculation unit for training a function based on the training module image data, the training patient image data, and the training differential image data, and a fourth training interface for providing the trained function.

A computer-implemented method for providing a trained function in order to generate patient movement data is also provided. This method includes receiving training adjustment data and receiving training patient movement data. The training patient movement data is, for example, linked to the training adjustment data. The method also includes training a function based on the training patient movement data and the training adjustment data, and providing the trained function in order to generate patient movement data.

The training adjustment data is, for example, data that only images a region of the patient incompletely (e.g., with gaps). The training adjustment data is, for example, data that only images a region of the patient completely (e.g., without gaps).

For example, the training adjustment data and the training patient movement data are time-dependent data. For example, the training adjustment data and the training patient movement data form a movement of the patient.

The trained function may be based on a neural network (e.g., a convolutional neural network (CNN) or a deep convolutional neural network).

For example, a training system that includes a first training interface for receiving training adjustment data, and a second interface for receiving training patient movement data is provided. The training system also includes a training calculation unit for training a function based on the training adjustment data and the training patient movement data, and a third training interface for providing the trained function.

An imaging apparatus (e.g., a magnetic resonance apparatus) that is configured to carry out a previously described method with the imaging apparatus in order to determine a patient movement during a medical imaging measurement is provided. For example, the imaging apparatus includes one or more cameras for acquiring reference image data and/or patient image data. For example, the imaging apparatus includes a system control unit for determining the patient movement and/or for creating a reference model and/or for creating adjustment data with the aid of acquired data. For example, the imaging apparatus includes one or more modules that are configured to partially cover the body region of the patient during the acquisition of patient image data.

A head coil, into which a miniature camera for acquiring image data of a face of a patient is integrated, is also provided.

A computer program product that includes a program and is directly loadable into a memory store of a programmable system control unit of an imaging apparatus (e.g., of a magnetic resonance apparatus) is provided. The computer program product includes program means (e.g., libraries and auxiliary functions) in order to carry out a method for determining a patient movement during a medical imaging measurement with the imaging apparatus when the computer program product is executed in the system control unit of the imaging apparatus. The computer program product may, for example, include an item of software with a source code that is still to be compiled and linked or is only to be interpreted, or an executable software code that, for execution, is to only be loaded into the system control unit. Using the computer program product, the method may be performed rapidly, exactly reproducibly, and robustly. The computer program product is configured so that the computer program product performs the method acts according to one or more of the present embodiments by the system control unit. The system control unit is to have the pre-conditions in each case such as, for example, a suitable working memory store, a suitable graphics card, or a suitable logic unit so that the respective method acts may be carried out efficiently. The computer program product is stored, for example, on a network or server, from where the computer program product may be loaded into the processor of a local system control unit that may be directly connected to, or configured as part of, the imaging apparatus.

Control information of the computer program product may be stored on an electronically readable data carrier (e.g., a non-transitory computer-readable storage medium). The control information of the electronically readable data carrier may be configured so that the electronically readable data carrier carries out a method of one or more of the present embodiments when the data carrier is used in a system control unit of an imaging apparatus. Examples of electronically readable data carriers are a DVD, a magnetic tape, or a USB stick, on which electronically readable control information (e.g., software) is stored. If this control information is read from the data carrier and stored in a system control unit of the imaging apparatus, all the embodiments of the above-described methods may be carried out. The present embodiments may therefore also proceed from the aforementioned computer-readable medium and/or the aforementioned electronically readable data carrier.

BRIEF DESCRIPTION OF THE DRAWINGS

Further advantages, features, and details are disclosed in the exemplary embodiments described below and by reference to the drawings. Parts that correspond to one another are provided with the same reference signs in all the figures, in which.

DETAILED DESCRIPTION

Figure 1:
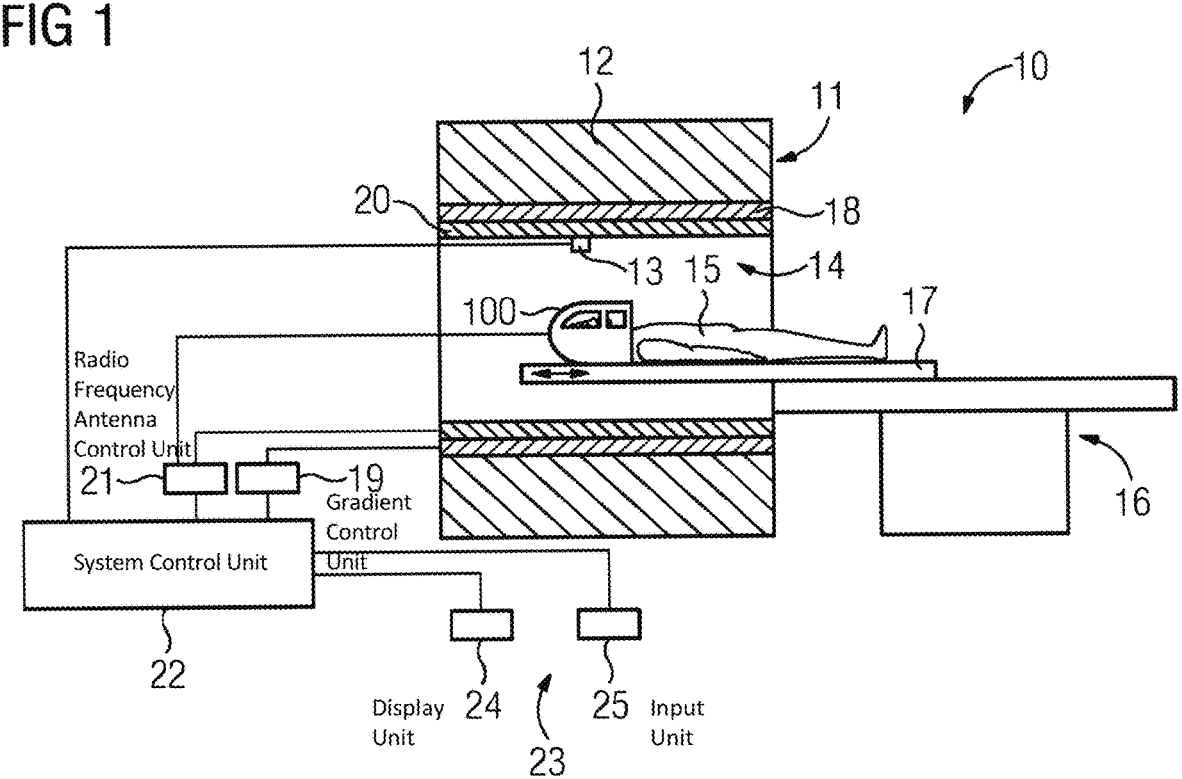
FIG. 1 shows one embodiment of a magnetic resonance apparatus with a head coil and a camera.

FIG. 1 shows, by way of example, a schematic representation of one embodiment of a magnetic resonance apparatus 10 for an imaging apparatus. The magnetic resonance apparatus 10 includes a magnet unit 11 that has a main magnet 12 for generating a strong and, for example, temporally constant main magnetic field. The magnetic resonance apparatus 10 also includes a patient receiving region 14 for receiving a patient 15. In the present exemplary embodiment, the patient receiving region 14 is configured to be cylindrical and surrounded in a cylindrical manner in a peripheral direction by the magnet unit 11. In principle, however, the patient receiving region 14 may have a different design. The patient 15 may be moved into the patient receiving region 14 by a patient support apparatus 16 of the magnetic resonance apparatus 10. To this end, the patient support apparatus 16 has a patient couch 17 configured movably within the patient receiving region 14.

The magnet unit 11 also has a gradient coil unit 18 for generating magnetic field gradients that are used during imaging for spatial encoding. The gradient coil unit 18 is controlled by a gradient control unit 19 of the magnetic resonance apparatus 10. The magnet unit 11 further includes a radio frequency antenna unit 20 that, in the present exemplary embodiment, is embodied as a body coil that is fixedly integrated into the magnetic resonance apparatus 10. The radio frequency antenna unit 20 is configured to excite atomic nuclei that develop in the main magnetic field generated by the main magnet 12. The radio frequency antenna unit 20 is controlled by a radio frequency antenna control unit 21 of the magnetic resonance apparatus 10 and radiates radio frequency pulses into an examination space, which is essentially formed by a patient receiving region 14 of the magnetic resonance apparatus 10. The radio frequency antenna unit 20 is also embodied to receive magnetic resonance signals. The magnetic resonance apparatus also has a module in the form of a head coil 100 that is arranged around the head of the patient 15. The head coil 100 is a local coil that is embodied to emit radio frequency pulses and/or to receive magnetic resonance signals.

In order to control the main magnet 12 and the radio frequency antenna control unit 21, the gradient control unit 19 and the magnetic resonance apparatus 10, respectively, have a system control unit 22. The system control unit 22 controls a medical imaging measurement of the magnetic resonance apparatus 10, such as, for example, the implementation of a predetermined imaging sequence. The system control unit 22 also includes an evaluation unit (not shown in more detail) for evaluating medical imaging data that is acquired in the form of, for example, magnetic resonance signals during the magnetic resonance examination. The system control unit 22 also includes a memory store, in which a program may be loaded directly, in order, for example, to carry out one of the methods described below to determine a patient movement, if the program is executed in the system control unit 22 of the magnetic resonance apparatus 10.

The magnetic resonance apparatus 10 includes a user interface 23 that is connected to the system control unit 22. Control information such as, for example, imaging parameters, and reconstructed magnetic resonance images may be indicated on a display unit 24 (e.g., on at least one monitor) of the user interface 23 for a medical operator. The user interface 23 has an input unit 25, by which information and/or parameters may be input by the medical operator during a measuring process.

The magnetic resonance apparatus further includes a camera 13 that is arranged on the interior of the magnet unit 11. The camera 13 is configured to detect image data and to transfer the image data to the system control unit 22. For example, the camera 13 may receive image data from the region of the head of the patient 15. The head coil 100 covers part of the head during the medical imaging measurement, so that the image data partially describes the head coil and partially the head (e.g., the face) of the patient.

Figure 2:
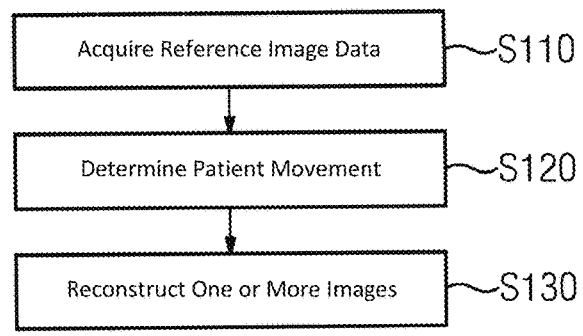
FIG. 2 shows a block diagram of a first embodiment of a method for determining a patient movement during a medical imaging measurement with an imaging apparatus.

The magnetic resonance apparatus is configured to carry out a method for determining a patient movement during a medical imaging measurement with the magnetic resonance apparatus. One such method is shown by way of example in FIGS. 2 and 3.

In S110, reference image data of a body region (e.g., the head region) of the patient 15 is acquired.

In S120, the patient movement is determined with the aid of the reference image data. The body region is, for example, a face of the patient, and the reference image data of the body region of the patient is acquired by a miniature camera arranged in a body coil.

In S130, one or more images of the patient are reconstructed in the form of magnetic resonance images based on the acquired magnetic resonance signals and the determined movement of the head.

Figure 3:
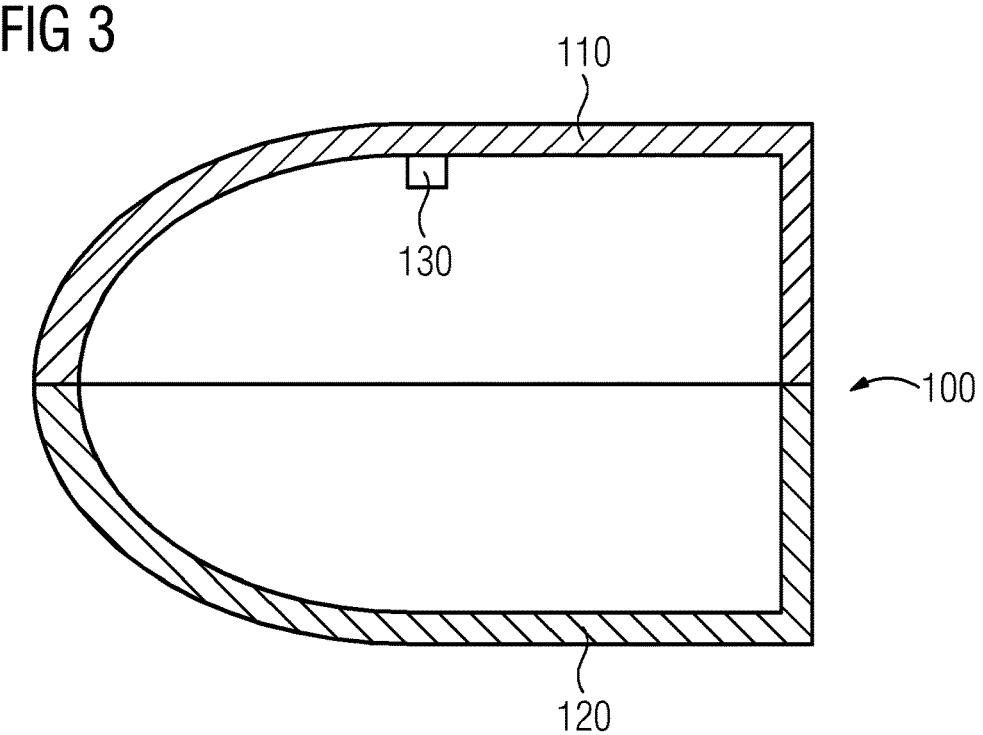
FIG. 3 shows one embodiment of a head coil with a mini camera.

FIG. 3 shows a head coil 100, into which a miniature camera 130 (e.g., an optical camera) is integrated in order to acquire image data of a face of a patient 15. The head coil 100 includes, for example, a top part 110 and a bottom part 120, on which the head of the patient 15 is supported. The miniature camera 130 is arranged on the interior of the top part and has a field of vision that is sufficiently large to acquire the face of the patient 15.

Figure 4:
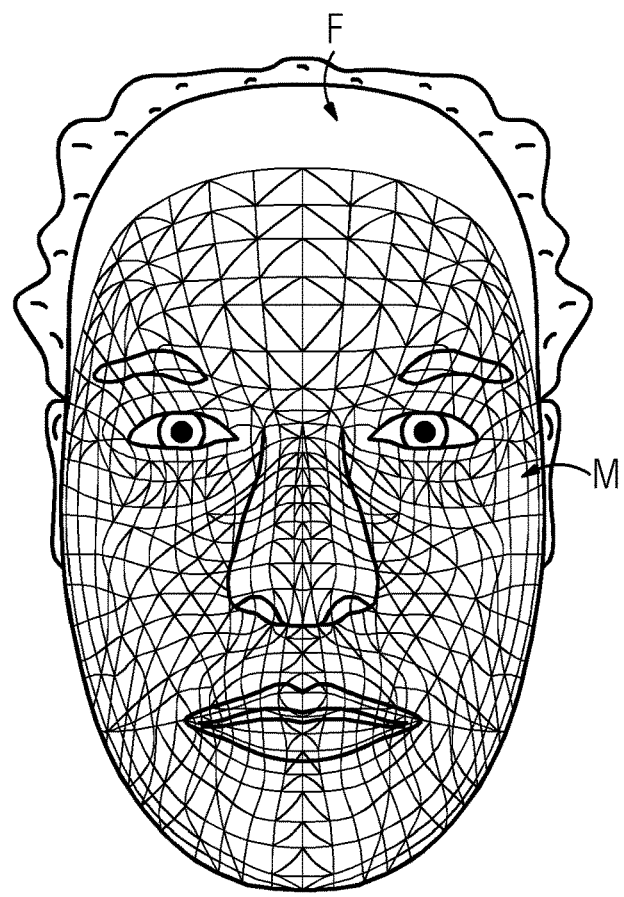
FIG. 4 shows a face of a patient with a lattice network describing the surface of the face.

FIG. 4 shows a face F of a patient 15. Depth images of the face F may be recorded in real time with the aid of the miniature camera 130. A three-dimensional lattice model M of the face F may be determined from the depth images, for example. The position and/or the movement of the head may be identified in real time from the depth images and/or the lattice model M. In this case, applying field markers to the face of the patient 15 may be dispensed with. The identified movement may be used, for example, to correct the movement.

Figure 5:
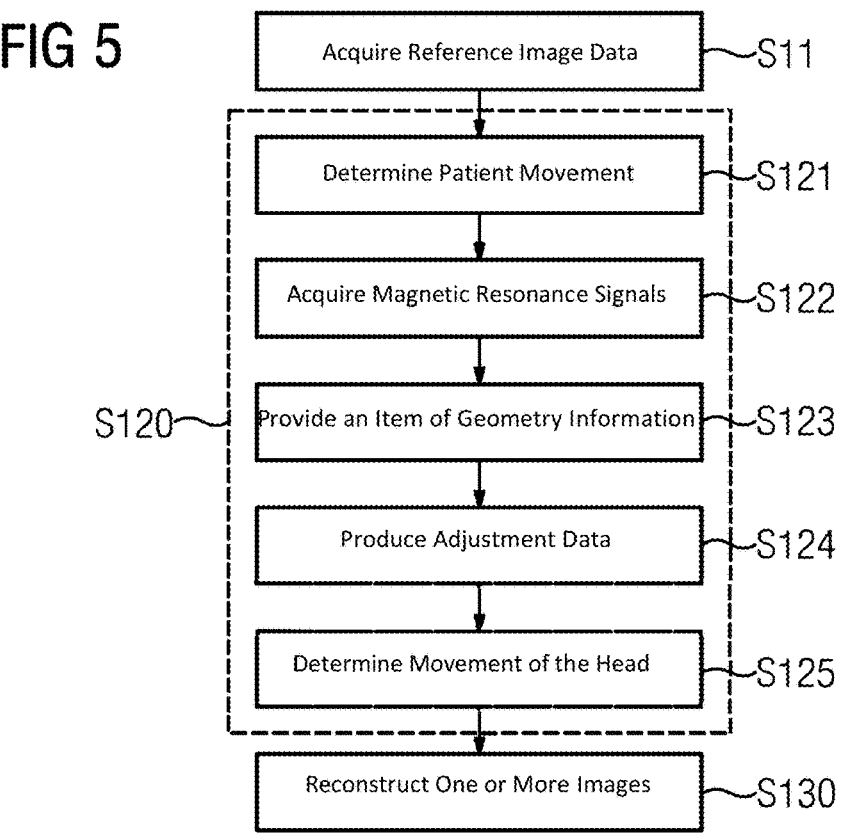
FIG. 5 shows a block diagram of a second embodiment of a method for determining a patient movement during a medical imaging measurement with an imaging apparatus.

FIG. 5 shows a further exemplary embodiment of a method for determining a patient movement during a medical imaging measurement with the magnetic resonance apparatus 10. In S121, a reference model of the head region of the patient 15 is produced when the patient movement is determined with the aid of the reference image data in S120.

For example, the production of the reference model of the head region of the patient 15 in S121 may involve, as shown by FIG. 4, the face F of the patient 15 being recorded (e.g., as depth image) as reference image data before the medical imaging measurement. The reference image data may be recorded with the camera 13, for example, before the top part 110 of the head coil 110 is assembled. The reference image data may also be acquired by another camera, for example, which is located outside of the measuring region of the magnetic resonance apparatus 10. A three-dimensional model of the face F may be produced from the recorded reference image data.

In S122, magnetic resonance signals as medical imaging data and patient image data of a part of the head region of the patient 15 are acquired during the medical imaging measurement. The head coil 100 partially covers the head region of the patient 15. The patient image data may be acquired by the camera 13, for example.

Figure 6:
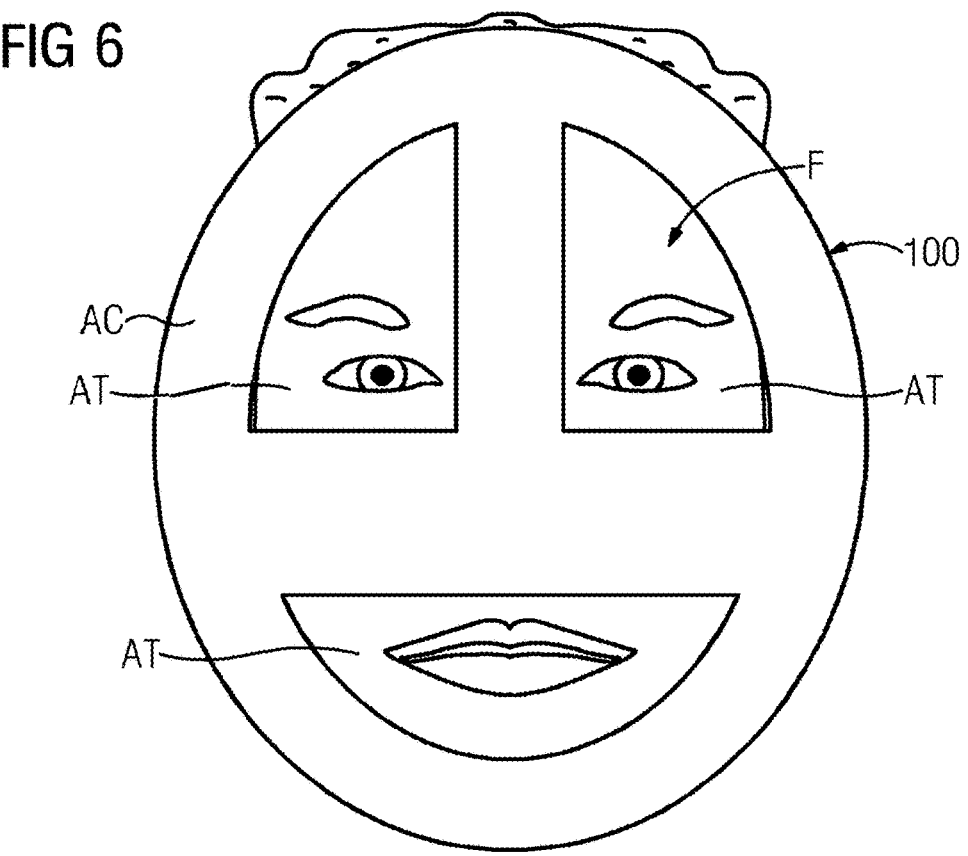
FIG. 6 shows a face of a patient that is partially covered by a head coil.

A partial coverage of the head region of the patient 15 by the head coil 100 is shown by way of example in FIG. 6. The top part 110 of the head coil 100 covers, in a subregion AC, the face F of the patient 15, while in a subregion AT, the face F of the patient 15 is acquired. For example, during the medical imaging measurement, the patient image data may emerge as a continuous depth image (e.g., as a video with a repetition frequency of 60 Hz) of the patient 15 and the head coil of the camera 13.

Figure 7:
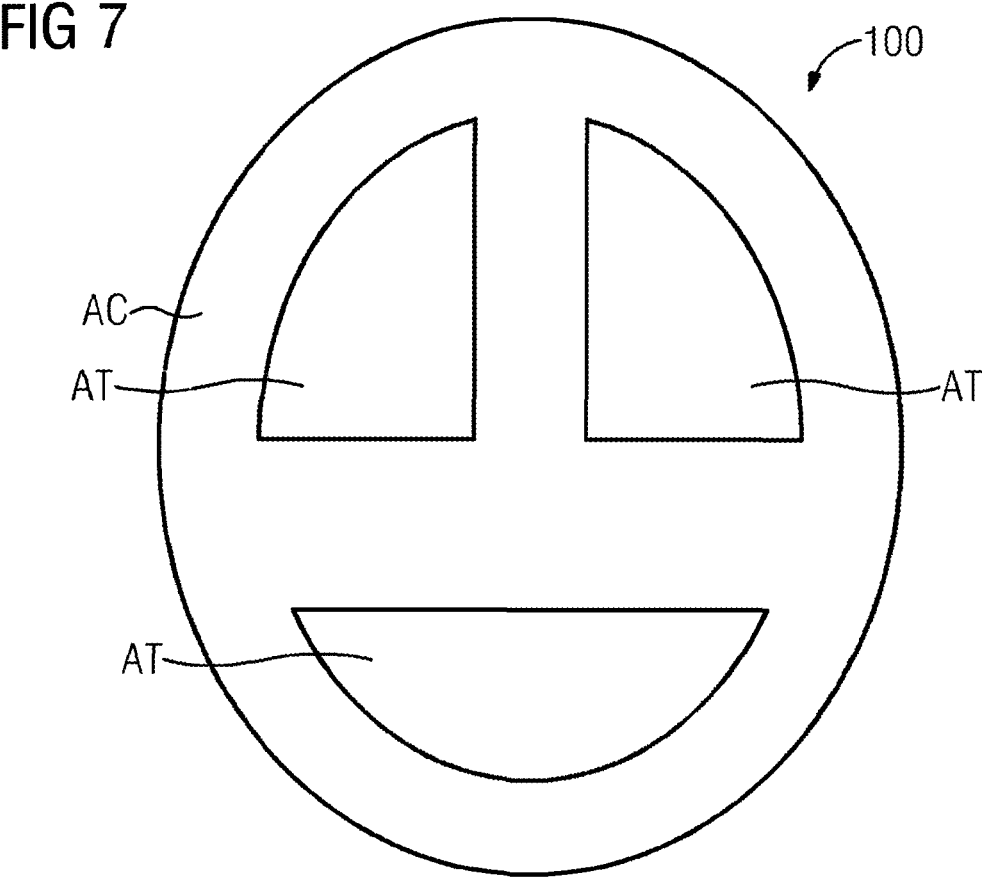
FIG. 7 shows a head coil that has covering and transparent regions.

In S123, an item of geometry information of the head coil 100 is provided. This may include, for example, an acquisition of module image data of the module of the imaging apparatus and/or a retrieval of geometric data of the module from a database. By way of example, geometry information of a head coil 100 is shown in FIG. 7.

The module image data may be recorded with the camera 13, for example, if the patient 15 is still not supported in the head coil 100. Module image data may be recorded as a mask depth image, for example.

The geometry information may exist as geometric data of the module (e.g., as CAD data). For example, the magnetic resonance apparatus 10 is embodied to identify a type of the module of the magnetic resonance apparatus 10 (e.g., a local coil type or a type of head coil 100). A corresponding item of geometry information may be provided as a function of the identified type of module. Different module forms may be taken into account, for example. The type of module may be identified, for example, by reading out a memory store (e.g., EEPROM) of the module.

In S124, adjustment data is produced from the patient image data with the aid of the geometry information. The geometry information may be used, for example, as a mask. In this way, differential image data is produced from the geometry information of the module and the patient image data, for example. For example, a mask depth image of the module (e.g., of the head coil 100) may be subtracted from the continuous depth image, so that only segments (e.g., face segments) of the patient 15 remain.

The differential image data may be generated, for example, by applying a function trained by machine learning to the geometry information of the module and the patient image data.

In S125, a movement of the head (e.g., of the face) of the patient 15 is determined by adjusting the adjustment data to the reference model.

The determination of the patient movement by adjusting the adjustment data to the reference model may involve applying a function trained by machine learning to the adjustment data, where patient movement data is generated.

For example, a video of the remaining segments of the patient 15 may be fitted on the full reference model. The entire face field may therefore only be reconstructed based on the remaining segments.

Figure 8:
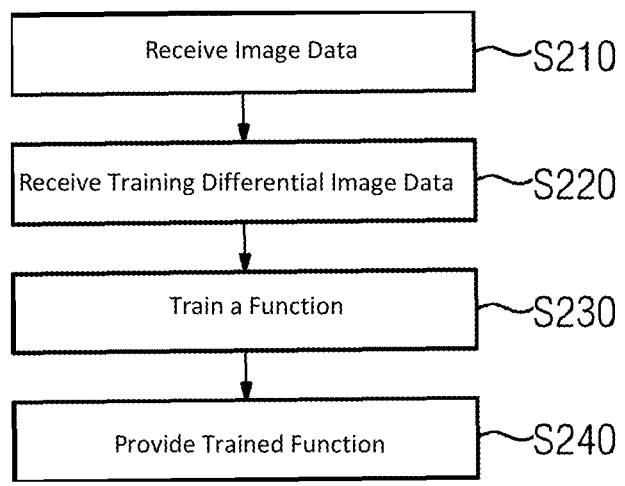
FIG. 8 shows a block diagram of one embodiment of a computer-implemented method for providing a trained function to generate differential image data.

FIG. 8 shows a schematic representation of a computer-implemented method for providing a trained function in order to generate differential image data.

In S210, training module image data and training patient image data are received. In S220, training differential image data is received. The training differential image data is linked with the training module image data and training patient image data.

In S230, a function is trained based on the training module image data, the training patient image data, and the training differential image data. In 240, a trained function is provided to generate differential image data.

Figure 9:
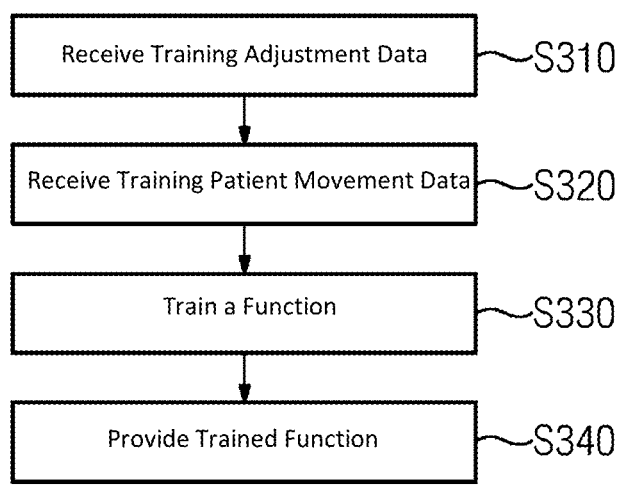
FIG. 9 shows a block diagram of an embodiment of a computer-implemented method for providing a trained function for generating patient movement data.

FIG. 9 shows a schematic representation of a computer-implemented method for providing a trained function in order to generate patient movement data.

In S310, training adjustment data is received. In S320, training patient movement data is received. The training patient movement data is linked to the training adjustment data.

In S330, a function is trained based on the training patient movement data and the training adjustment data. In S340, a trained function is provided to generate patient movement data.

The methods and devices described above in detail are exemplary embodiments that may be modified by a person skilled in the art in a wide variety of ways without departing from the scope of the invention. In addition, the use of the indefinite article "a" or "an" does not preclude the relevant features also being present plurally. Similarly, the expression "unit" does not exclude the relevant components consisting of a plurality of cooperating subcomponents that may also be spatially distributed if required.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A method for determining a patient movement during a medical imaging measurement with an imaging apparatus, the method comprising:
   acquiring reference image data of a body region of a patient;
   acquiring patient image data of a part of the body region of the patient during the medical imaging measurement;
   providing geometric data for a module of the imaging apparatus, wherein the module partially covers the body region of the patient during the acquisition of the patient image data;
   determining, by a processor, adjustment data using the geometric data as a mask, determining the adjustment data comprising producing the adjustment data from the patient image data, producing the adjustment data from the patient image data comprising generating differential data from the geometric data for the module of the imaging apparatus and the patient image data, generating the differential data from the geometric data for the module of the imaging apparatus and the patient image data comprising applying a function trained by machine learning to the geometric data for the module of the imaging apparatus and the patient image data;
   determining, by the processor, the patient movement based on the reference image data and the differential data; and
   reconstructing one or more images of the patient based on the acquired patient image data and the determined patient movement,
   wherein the function is trained by machine learning based on training module image data of the module.

2. The method of claim 1, wherein the image apparatus is a magnetic resonance apparatus.

3. The method of claim 1, further comprising:
   producing a reference model of the body region of the patient based on the reference image data, and
   wherein determining the patient movement comprises fitting the adjustment data to the reference model.

4. The method of claim 3, wherein determining the patient movement by fitting the adjustment data to the reference model comprises applying a function trained by machine learning to the adjustment data, such that the patient movement data is generated.

5. The method of claim 1, wherein providing the item of geometry information of the module of the imaging apparatus comprises providing an item of geometry information of a local coil.

6. The method of claim 1, wherein the body region of the patient is a head region of the patient, and
   wherein the module of the imaging apparatus is a head coil.

7. The method of claim 1, wherein providing the item of geometry information of the module of the imaging apparatus comprises acquiring module image data of the module of the imaging apparatus, recalling geometric data of the module from a database, or a combination thereof.

8. The method of claim 1, wherein the body region is a face of the patient, and
   wherein the acquisition of the reference image data of the body region of the patient takes place using a camera arranged in a head coil.

9. The method of claim 1, wherein the determination of the patient movement takes place in real time during the medical imaging measurement.

10. The method of claim 1, wherein no external marker is attached to the patient during the medical imaging measurement.

11. The method of claim 1, wherein the module of the imaging apparatus is a local coil, and
    wherein the item of geometry information is geometric data, the geometric data being computer-aided design (CAD) data.

12. The method of claim 1, wherein providing the item of geometry information of the module of the imaging apparatus comprises:
    identifying a type of the module of the imaging apparatus; and
    providing the item of geometry information based on the identified type of the module of the imaging apparatus.

13. The method of claim 1, wherein providing the item of geometry information of the module of the image apparatus comprises:
    acquiring module image data of the module of the imaging apparatus;
    retrieving geometric data of the module of the imaging apparatus from a database; or
    a combination thereof.

14. A computer-implemented method for providing a trained function, the computer-implemented method comprising:
    receiving training module image data and training patient image data, the training module image data being of a module of an imaging apparatus and the training patient image data being of a region of a patient, the training module image data representing geometric data for the module of the imaging apparatus;
    receiving training differential image data, wherein the training differential image data is associated with the training module image data and the training patient image data;
    training, by a processor, a function based on the training module image data, the training patient image data, and the training differential image data;
    providing the trained function, which is operable to generate differential image data;
    acquiring patient image data during a medical imaging measurement;
    generating the differential image data using the acquired patient image data and the provided trained function; and
    reconstructing one or more images of the patient using the acquired patient image data and the generated differential image data.

15. An imaging apparatus comprising:
    an imaging device configured to acquire reference image data of a body region of a patient; and
    a processor configured to:
       acquire patient image data of a part of the body region of the patient during a medical imaging measurement;

identify geometric data for a module of the imaging apparatus, wherein the module partially covers the body region of the patient during the acquisition of the patient image data;

determine adjustment data using the geometric data as a mask, the determination of the adjustment data comprising production of the adjustment data from the patient image data, the production of the adjustment data from the patient image data comprising generation of differential data from the geometric data for the module of the imaging apparatus and the patient image data, the generation of the differential data from the geometric data for the module of the imaging apparatus and the patient image data comprising application of a function trained by machine learning to the geometric data for the module of the imaging apparatus and the patient image data;

determine a patient movement during the medical imaging measurement with the imaging apparatus, the determination of the patient movement comprising determination of the patient movement based on the reference image data and the differential data; and reconstruct one or more images of the patient based on the identified patient image data and the determined patient movements, wherein the function is trained by machine learning based on training module image data of the module.

16. The imaging apparatus of claim 15, wherein the imaging device is an optical camera.

17. The imaging apparatus of claim 15, wherein the module is a head coil, the head coil comprising:

a housing; and a camera integrated into the housing, the camera being configured to acquire image data of a face of a patient.

18. A non-transitory computer-readable storage medium that stores instructions executable by a programmable system control unit of an imaging apparatus to determine a patient movement during a medical imaging measurement with an imaging apparatus, the instructions comprising:

acquiring reference image data of a body region of a patient;

acquiring patient image data of a part of the body region of the patient during the medical imaging measurement;

providing geometric data for a module of the imaging apparatus, wherein the module partially covers the body region of the patient during the acquisition of the patient image data;

determining, by a processor, adjustment data using the geometric data as a mask, determining the adjustment data comprising producing the adjustment data from the patient image data, producing the adjustment data from the patient image data comprising generating differential data from the geometric data for the module of the imaging apparatus and the patient image data, generating the differential data from the geometric data for the module of the imaging apparatus and the patient image data comprising applying a function trained by machine learning to the geometric data for the module of the imaging apparatus and the patient image data;

determining, by the processor, the patient movement based on the reference image data and the differential data; and reconstructing one or more images of the patient based on the acquired patient image data and the determined patient movement, wherein the function is trained by machine learning based on training module image data of the module.

* * * * *